United States Patent
Harboe et al.

[11] Patent Number: 6,063,063
[45] Date of Patent: May 16, 2000

[54] CATHETER WITH AN OPEN/CLOSING MECHANISM

[75] Inventors: Henrik Harboe; Erik Othel-Jacobsen, both of Kvistgaard, Denmark

[73] Assignee: Engineers & Doctors A/S, Denmark

[21] Appl. No.: 08/981,771

[22] PCT Filed: Jun. 7, 1996

[86] PCT No.: PCT/DK96/00251

§ 371 Date: Dec. 5, 1997

§ 102(e) Date: Dec. 5, 1997

[87] PCT Pub. No.: WO96/41653

PCT Pub. Date: Dec. 27, 1996

[30] Foreign Application Priority Data

Jun. 8, 1995 [DK] Denmark .................................. 0648/95

[51] Int. Cl.[7] .............................. A61M 11/00; A61M 5/00
[52] U.S. Cl. .............................. 604/256; 604/93; 604/264
[58] Field of Search .............................. 604/93, 246, 256, 604/263, 265, 268, 264, 275, 278, 280, 323, 349, 350; 600/29, 30, 32; 220/339; 128/912

[56] References Cited

U.S. PATENT DOCUMENTS

| | | |
|---|---|---|
| 3,794,042 | 2/1974 | De Klotz et al. . |
| 4,685,901 | 8/1987 | Parks . |
| 4,822,333 | 4/1989 | Lavarenne .................................. 600/30 |
| 5,087,252 | 2/1992 | Denard . |
| 5,234,409 | 8/1993 | Goldberg et al. . |
| 5,385,372 | 1/1995 | Utterberg .................................. 285/332 |
| 5,674,209 | 10/1997 | Yarger .................................. 604/283 |
| 5,817,067 | 10/1998 | Tsukada .................................. 604/256 |

FOREIGN PATENT DOCUMENTS

| | | |
|---|---|---|
| 0 437 291 A1 | 7/1991 | European Pat. Off. . |
| 1 491 711 | 4/1969 | Germany . |
| 2 230 702 | 10/1990 | United Kingdom . |
| WO 91/14473 | 10/1991 | WIPO . |

*Primary Examiner*—Wynn Wood Coggins
*Assistant Examiner*—Michael J. Hayes
*Attorney, Agent, or Firm*—Brinks, Hofer, Gilson & Lione

[57] ABSTRACT

The invention relates to a catheter including a tubular part, a closure, a radially projecting part, and an operating handle. The tubular part has a proximal end and a distal end, at least one inlet opening at the proximal end and at least one outlet opening at the distal end. The closure is connected to the tubular part by a first hinge, with the closure extending beyond the first hinge. The radially projecting part projects from the tubular part. The operation handle is connected to the catheter by means of a second hinge at the end of the closure extension, and by means of a third hinge at the radially projecting part. The total length of the closure extension and the operation handle exceeds the rectilinear distance between the first and the third hinges. The catheter according to this invention provides a simple construction, which can be inserted and operated by one hand of the user and at a convenient site, not necessarily over a receptacle for urine or other bodily fluids. The opening/closing mechanism further gives the user the feeling of controlling the act of urination.

11 Claims, 4 Drawing Sheets

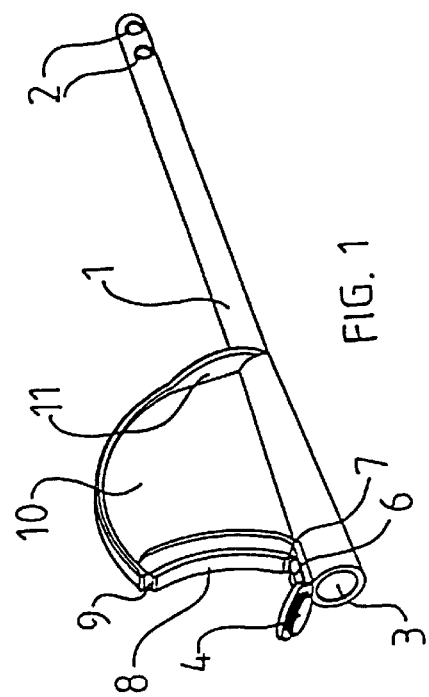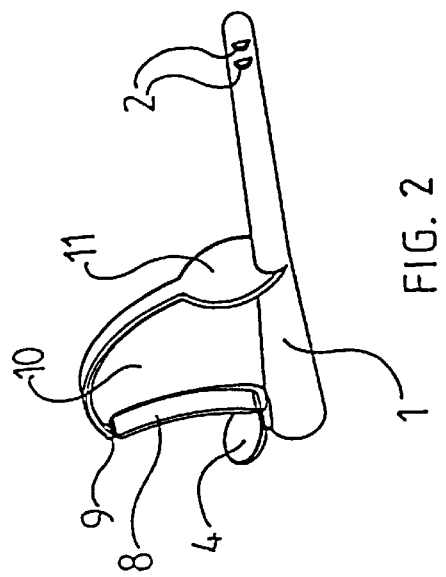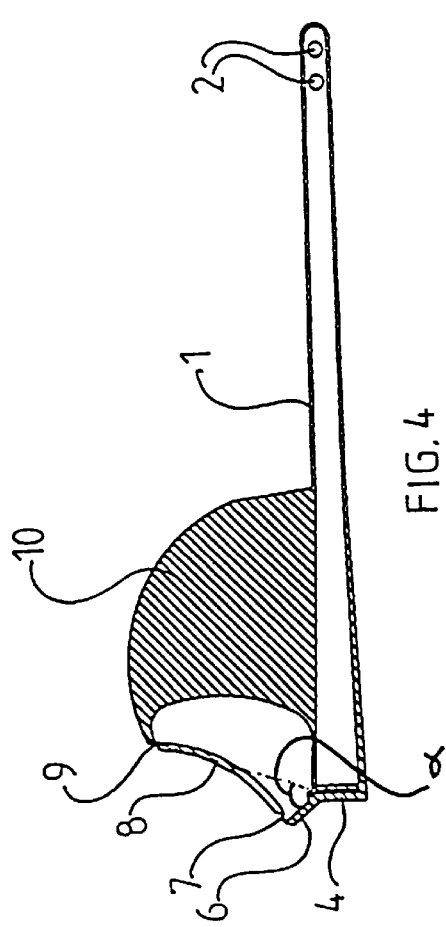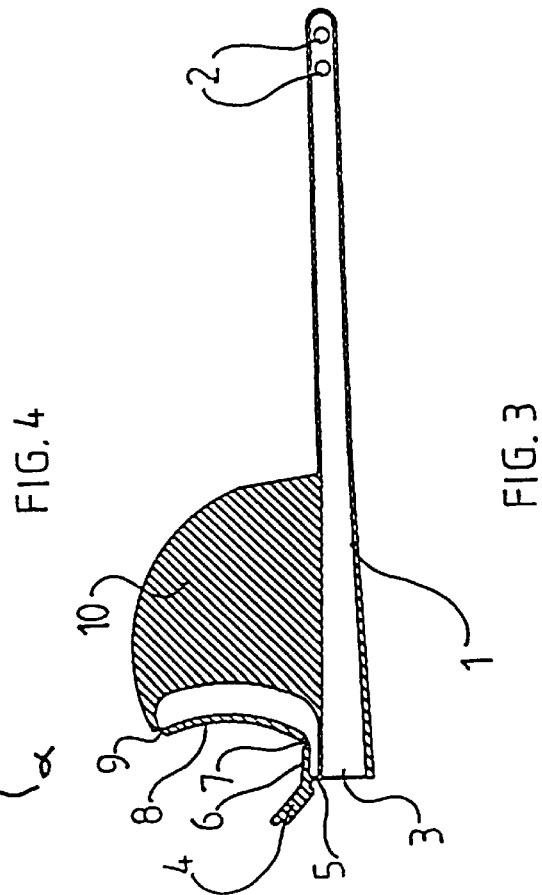

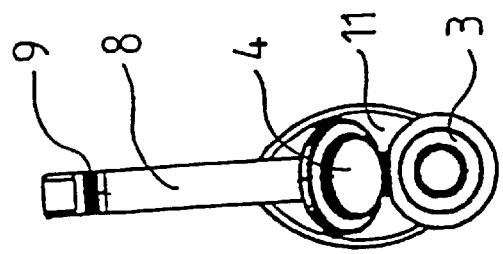
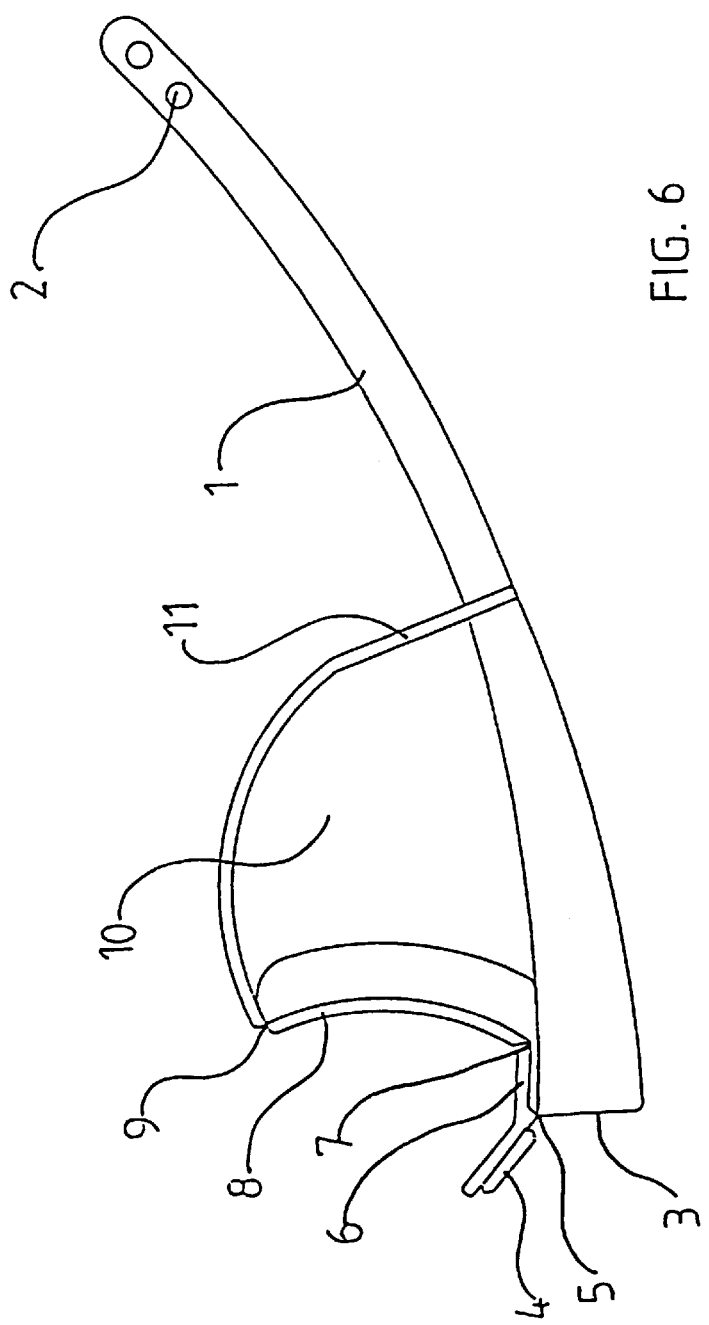

CATHETER WITH AN OPEN/CLOSING MECHANISM

BACKGROUND OF THE INVENTION

The invention relates to a catheter comprising a tubular part having a proximal end and a distal end, at least one inlet opening at the proximal end, at least one outlet opening at the distal end, and comprising a closure for closing the at least one outlet opening.

Such catheters are used for numerous purposes within the field of medical care. One area towards which the present invention is especially directed is the urology area.

In case of a urethral disorder in the form of a urethral stricture, i.e. prostatic hypertrophy in a male patient, it is required to use a catheter in order to empty the urine bladder. The catheter is inserted into the urine bladder through the urethra.

From GE 2 230 702 an example of such a urethral catheter is known. Since there are no means provided for blocking the flowpath, it is obvious that the urine flow through the catheter will start as soon as the opening at the proximal end of the catheter enters the bladder.

This means that the insertion of the catheter must take place over a receptacle for the urine, which of course makes the use of the catheter difficult.

U.S. Pat. No. 3,794,042 discloses a urethral catheter/receptacle-construction for self-catheterization and comprising a valve for controlling the flow through the catheter and out into a receptacle. The valve is very complex and its operation requires two hands.

U.S. Pat. No. 5,087,252 discloses a catheter of the type described in the introductory part of the description. This previously known catheter comprises a complex closing mechanism having several parts. This means that the catheter manufacturing is time consuming and that the operation not always can be regarded as reliable.

SUMMARY OF THE INVENTION

The object of the present invention is to provide a catheter which is simple and at the same time allows for an easy and reliable operation by the user.

According to the invention this object is obtained with a catheter of the type mentioned in the introductory part and which is characterised in that the closure is connected to the tubular part by a first hinge, where a part of said closure extends beyond said first hinge, a in respect of the tubular part radially projecting part, an operation handle connected to the catheter by means of a second hinge at the end of the closure extension and a third hinge at the radially projecting part, the total length of closure extension and the operation handle exceeding the rectilinear distance between the first and the third hinges.

The catheter according to the invention provides a simple construction which can be inserted and operated by one hand of the user and at a convenient site, not necessarily over a receptacle for the urine or other body fluids. The opening/closing mechanism further gives the user the feeling of controlling the urination.

In a preferred embodiment of the catheter according to the invention the radially projecting part forms a handle for the insertion of the catheter and minimizes the risk of contamination of the tubular part. This feature facilitates the insertion of the catheter. Preferably the catheter comprises a stop plate for limiting the insertion distance of the catheter, which stop plate is advantageously constructed integrally with the handle. The stop plate prevents the user from inserting the catheter towards the opposing wall of the bladder and the thus inflicted discomfort is avoided.

The closure with its extension forms an essentially rigid part where, relative to a straight line between the hinge axis for the closure and the hinge axis at the radially projecting part in a closed position for the closure, the extension has a preferred angled configuration in the closing direction for the closure.

Preferably, the handle part connected at one side to the closure extension and at the other side to the radially projecting part has a length exceeding the rectilinear distance between the hinge axes at the locations in order to perform a spring action on closure extension hereby ensuring the closed position of the closure. The length of the handle bar is preferably sufficient to enable an opening angle where the closure is pivoted away from the flow path out through the outlet opening. In the preferred embodiment the handle part has a configuration which makes it flexible and elastically deformable between the extreme open and closed positions of the closure.

The handle part can obviously be constituted of several mutually hinged elements which at their outer ends are connected to the closure extension and the radially projecting part.

The catheter according to the invention is in a preferred embodiment constructed in a manner where the tubular part is curved according to the anatomy of the urethea especially the anatomy of the female urethea. This feature facilitates the insertion of the catheter. To further facilitate the insertion the outer surface of the tubular part is preferably covered with a hydrophilic material, or the entire catheter is made of a hydrophilic material. A biodegradable material is also desirable for the manufacture of such catheter.

The invention further relates to an opening/closing mechanism for a catheter comprising a base part with an outlet opening, a closure for closing the outlet opening which closure is connected to the base part.

According to the invention this mechanism is characterized in that the closure is connected to the base part by means of a first hinge where a part of said closure extends beyond said first hinge, a radially projecting part projecting from said base part, an operation handle connected to the closure extension by means of second hinge and to the radially projecting part by means of a third hinge, the total length of the closure extension and the operation handle exceeding the rectilinear distance between the first and the third hinges.

The base part can have either a tubular configuration for connection to the end region of a tubular catheter part or have a configuration complementary to the outer surface of a tubular catheter part.

Although the opening/closing mechanism described above primarily is intended for use in connection with a urology catheter as also described above it is obvious that this mechanism can be used in connection with other types of catheters, i.e. as suction catheters, to obtain an easy operable and reliable control mechanism for the control of fluids, such as air, in or out through an opening in the catheter.

BRIEF DESCRIPTION OF THE DRAWINGS

FIG. 1 shows in perspective a catheter,

FIG. 2 shows the catheter of FIG. 1 from a different angle,

FIG. 3 shows in section the catheter of FIGS. 1 and 2 with the valve in an open position, FIG. 4 shows in section the catheter of FIGS. 1 and 2 with the valve in a closed position, FIG. 5 shows the catheter of FIGS. 1 and 2 in an end view, FIG. 6 shows a catheter with a preferred curved shape.

DETAILED DESCRIPTION

Figure 8:
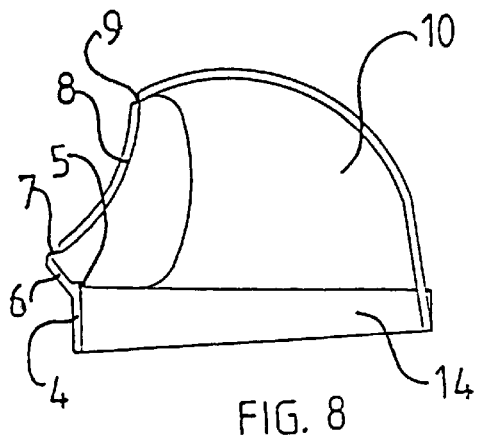
FIG. 8 shows the valve part of FIG. 7 with the valve in a closed position.

FIGS. 1 and 2 show in perspective view a urethral catheter comprising a tubular part 1 having at its proximal end radially directed inlet openings 2. The openings 2 are arranged with mutual distance in the axial direction so as to allow drainage from the urine bladder at different insertion lengths for the catheter. The tubular part has at the distal end a conical or funnelshaped configuration. At the distal end the tubular part 1 comprises an outlet opening 3 and at this end a closure 4 is connected pivotably to the tubular part 1 by means of a hinge 5. The closure comprises a part 6 which extends beyond the hinge 5. A radially projecting grip 10 is provided on the tubular part 1 near the distal end of this. Between the grip 10 and the closure extension 6 and by means of hinges 7 and 9 an operation handle 8 is provided, and at the end of the grip 10 facing the proximal end of the catheter a stop plate 11 is provided for limiting the insertion length of the catheter. All hinges are so-called film hinges formed integrally with the adjacent elements.

The opening/closure mechanism appears more clearly from FIGS. 4 and 3 which show the catheter in cross section with the closure in a closed and an open position, respectively. The closure with its extension forms an essentially rigid part where, relative to a straight line between the hinge axis for the closure and the hinge axis at the radially projecting part in a closed position for the closure, the extension has a preferred angled configuration with an angle α in the closing direction for the closure.

FIG. 5 is an end view of the catheter shown in FIGS. 1–4.

FIG. 6 shows a catheter with a curved configuration of the tubular part 1. The curvature of the tubular part corresponds to that of the female urethra and facilitates insertion.

Figure 9:
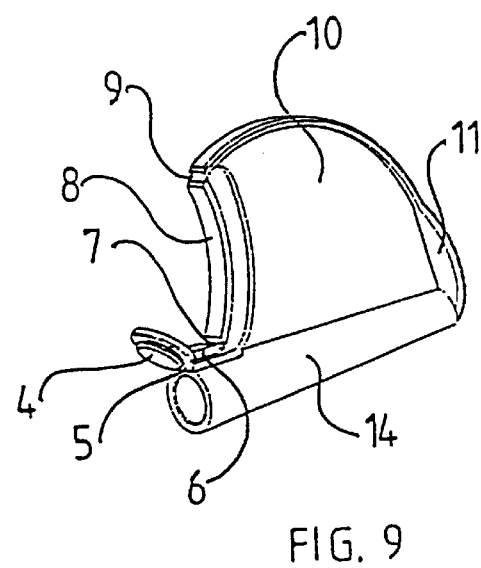
FIG. 9 shows in perspective view the valve part of FIGS. 7 and 8, FIGS. 10 and 11 demonstrate schematically the use of the catheter of FIGS. 1–5.
Figure 7:
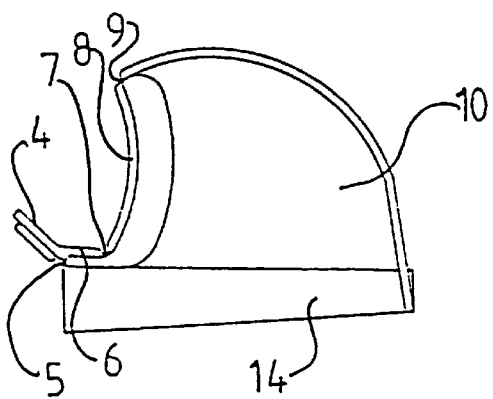
FIG. 7 shows a valve part adapted for connection to a tubular catheter part, and in an open position.

FIGS. 7–9 show an opening/closing mechanism adapted for connection to a tubular catheter part. The tubular part or base part 14 of the mechanism forms an extension of the catheter tube. By means of this mechanism it is possible to manufacture the catheter shown in FIGS. 1–6 as two separate parts which afterwards have to be joined together by means of gluing or welding, by a mechanical joint, such as a snap or thread connection means, or any other suitable means of joining. This opening/closing mechanism can of course find use in connection with other types of catheters in order to control the flow through an opening.

Figure 10:
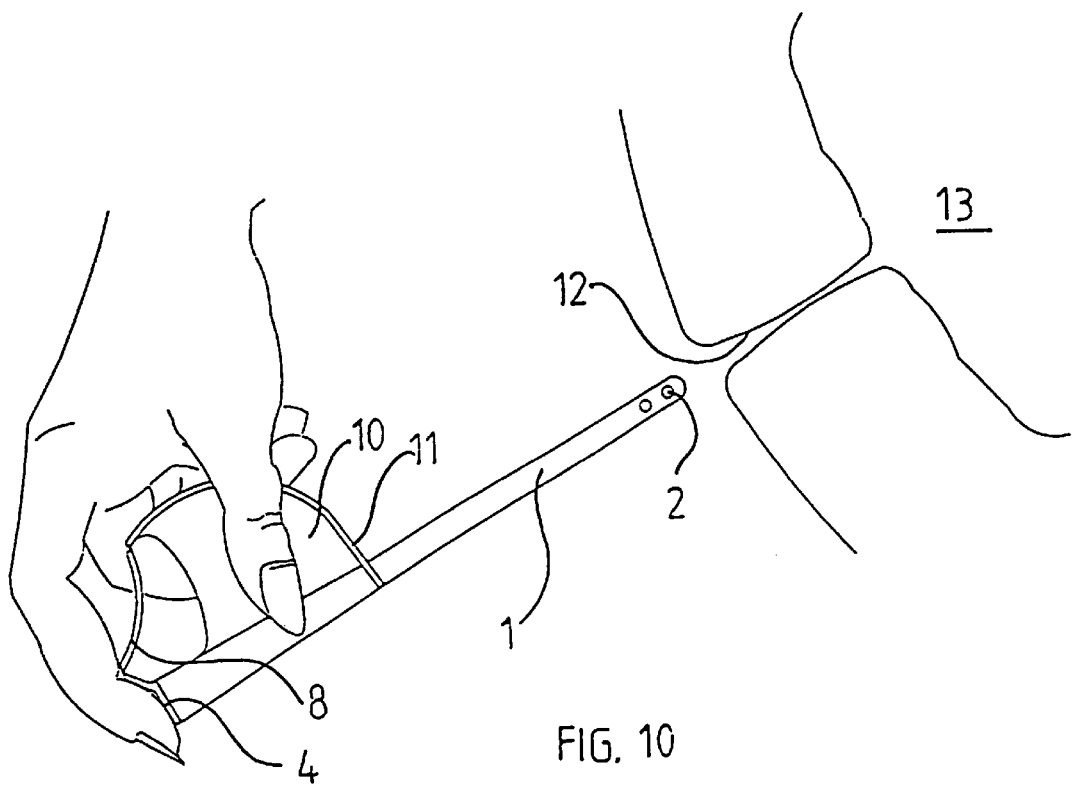
Figure 11:
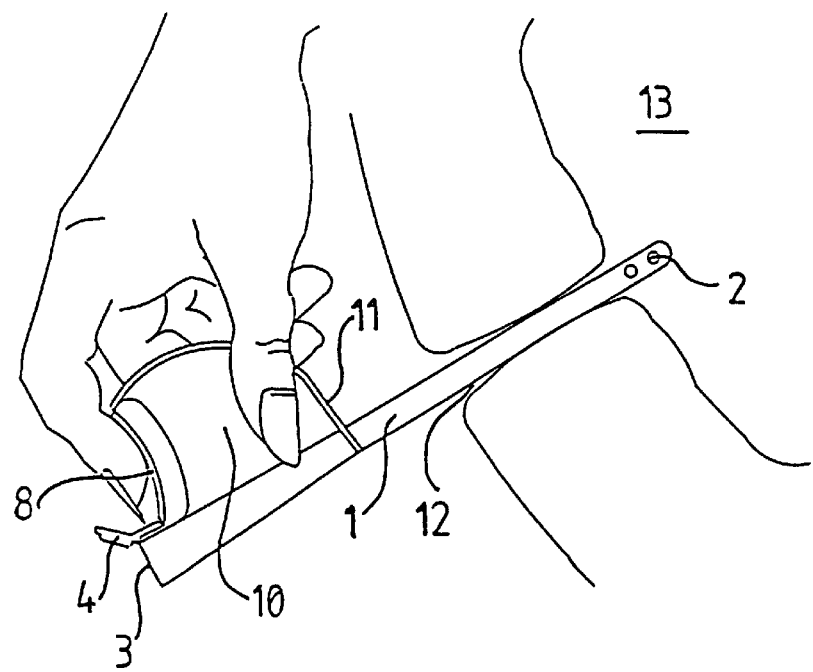

FIGS. 10 and 11 demonstrate schematically how the catheter is inserted into the urine bladder 13 through the urethra with the closure 4 in a position blocking the flowpath through the tubular part 1. After insertion the operation handle 8 is actuated to pivot the closure 4 away from the outlet opening 3. After having completed the drainage, the closure 4 can be pivoted back in the closed position to prevent dripping from the outlet opening 3.

The catheter according to the invention can be manufactured by injection moulding in one piece or in several pieces which are joined afterwards by i.a. gluing or welding, by a mechanical joint, such as a snap or thread connection means, or any other suitable means of joining. The holes, especially at the proximal end of the catheter, preferably have rounded edges in order to minimize the risk of irritating the tissue.

What is claimed is:

1. A catheter comprising a tubular part having a proximal end and a distal end, at least one inlet opening at the proximal end, at least one outlet opening at the distal end, and comprising a closure for closing the at least one outlet opening, the closure being connected to the tubular part by a first hinge, said closure having a closure extension extending beyond said first hinge, a radially projecting part projecting from said tubular part, and an operation handle being connected to the catheter by means of a second hinge at the end of the closure extension and by means of a third hinge at the radially projecting part, wherein the total length of the closure extension and the operation handle exceeds the rectilinear distance between the first and the third hinges.

2. A catheter according to claim 1, wherein the radially projecting part forms a handle for the insertion of the catheter.

3. A catheter according to claim 1, further comprising a stop plate for limiting the insertion distance of the catheter.

4. A catheter according to claim 3, wherein the stop plate is constructed integrally with the handle.

5. A catheter according to claim 1, wherein the tubular part is curved according to the anatomy of the urethra.

6. A catheter according to claim 1, wherein the outer surface of the tubular part is covered with a hydrophilic material.

7. A catheter according to claim 1, wherein the closure with its extension forms an essentially rigid part where, relative to a straight line between the hinge axis for the closure and the hinge axis at the radially projecting part in a closed position for the closure, the extension has a preferred angled configuration in the closing direction for the closure.

8. A catheter according to claim 1, wherein the handle part connected at one side to the closure extension and at the other side to the radially projecting part has a length exceeding the rectilinear distance between the hinge axes at the locations in order to perform a spring action on closure extension thereby ensuring the closed position of the closure.

9. An opening/closing mechanism for a catheter comprising a base part with an outlet opening, a closure for closing the outlet opening which closure is connected to the base part, the closure being connected to the base part by means of a first hinge where a part of said closure extends beyond said first hinge, a radially projecting part projecting from said base part, an operation handle being connected to the closure extension by means of second hinge and to the radially projecting part by means of a third hinge, the total length of the closure extension and the operation handle exceeding the rectilinear distance between the first and the third hinges.

10. A mechanism according to claim 9, wherein the base part has a tubular configuration adapted for connection to the end region of a tubular catheter extension.

11. A mechanism according to claim 9, wherein the base part is adapted for connection to an outer surface of a tubular catheter part by means of a complementary shaped outer surface of the base part.

* * * * *